US00PP08015P

United States Patent [19]

Falstad, III

[11] Patent Number: Plant 8,015

[45] Date of Patent: Oct. 27, 1992

[54] HOSTA PLANTAGINEA — WHITE MARGIN' VARIETY

[76] Inventor: Clarence H. Falstad, III, 152 Birchwood, Holland, Mich. 49423

[21] Appl. No.: 540,816

[22] Filed: Jun. 19, 1990

[51] Int. Cl.[5] ..... A01H 5/00

[52] U.S. Cl. ..... Plt./68.1

[58] Field of Search ..... Plt./68

*Primary Examiner*—Howard J. Locker

*Attorney, Agent, or Firm*—Waters & Morse

[57] ABSTRACT

A variety of *Hosta plantaginea* having leaves with a white margin.

2 Drawing Sheets

SUMMARY OF THE INVENTION

The new variety of Hosta is a tissue culture derived sport of the species *Hosta plantaginea*. I originally discovered the plant in a cultivated state as a sectorial chimera in some test tubes of tissue cultured *Hosta plantaginea* at a nursery in Zeeland, Mich. The plant, with its novel white variegation, has been produced in a stable periclinal form. The new variety is hereby named the 'White Margin' variety and is sold under the "White Shoulders" trademark.

A sexual propagation of the new cultivar by tissue culture as well as by rhizome division in a nursery in Zeeland, Mich., has conclusively shown that all characteristic and distinguishing features of the cultivar are faithfully transmitted or passed from one generation to the next by such means, and that the cultivar is stable.

BRIEF DESCRIPTION OF THE DRAWINGS

The invention is illustrated in the attached photographic drawings in which.

DETAILED DESCRIPTION OF PREFERRED EMBODIMENT

Figure 1:
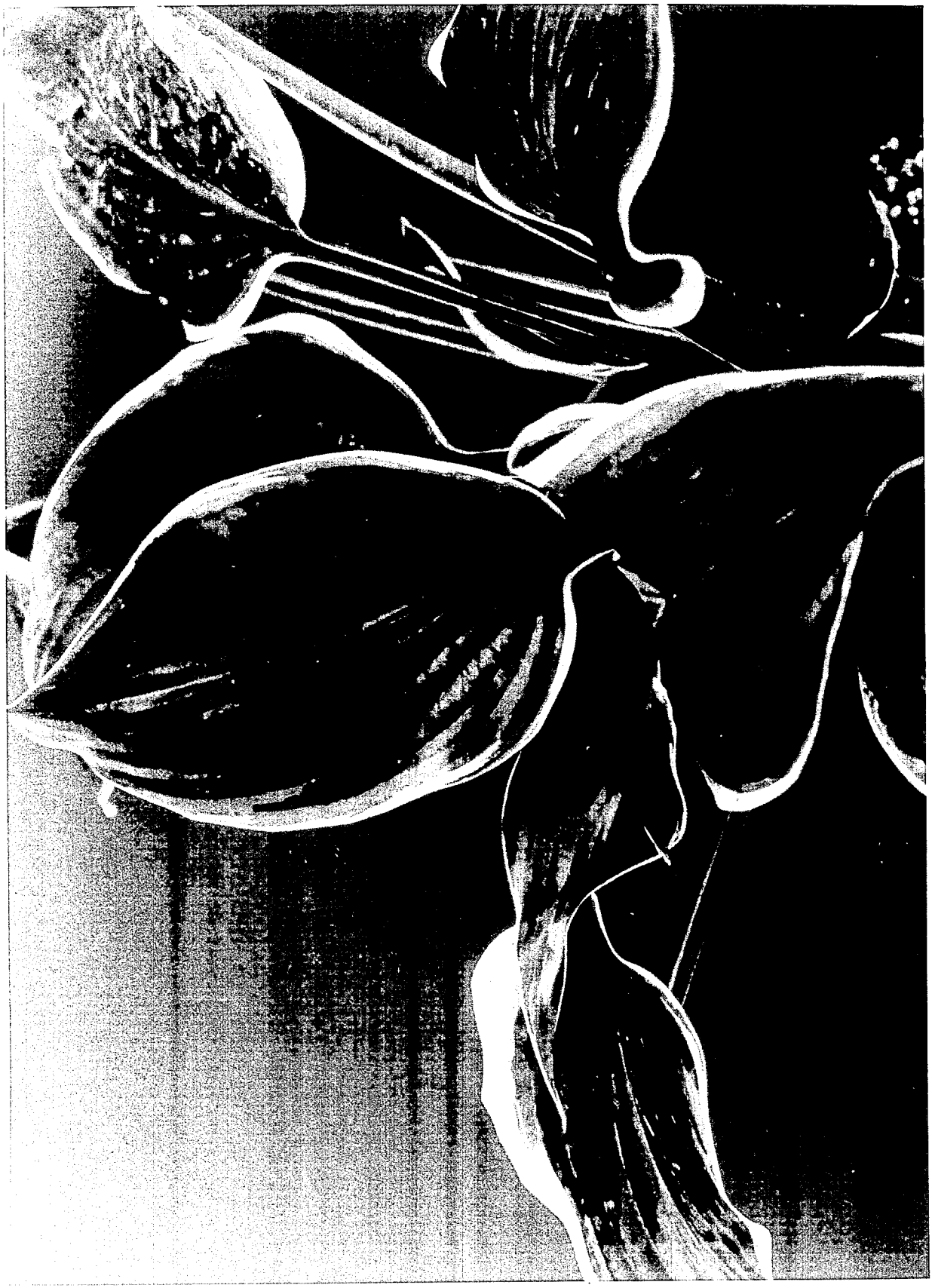
FIG. 1 shows the plant with a leaf having a narrow, white margin.
Figure 2:
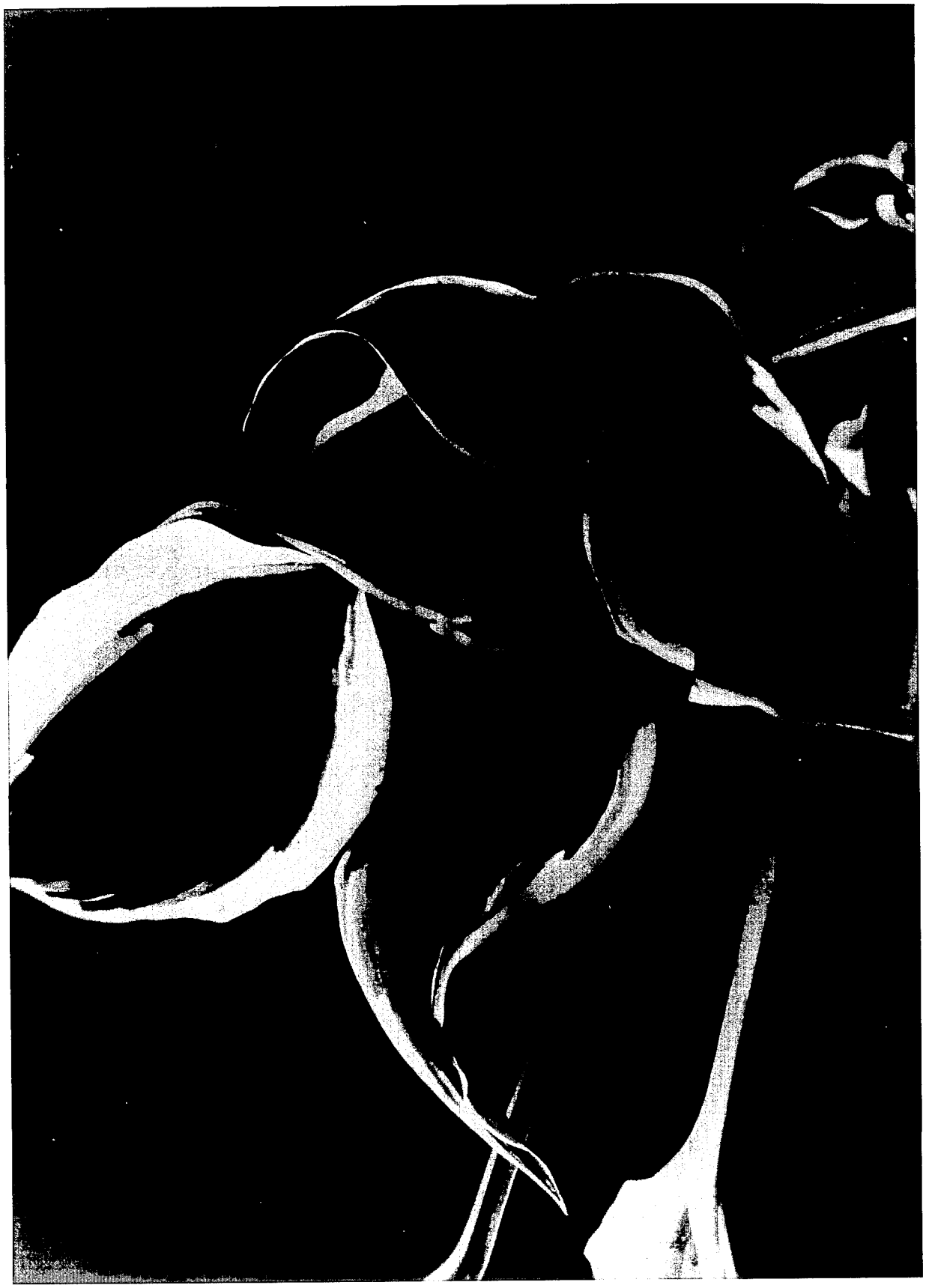
FIG. 2 shows the plant with a leaf having a wider, white margin.

The species *Hosta plantaginea* is a densely rhizomatous herbaceous perennial with a short subterranean stem and has petioled, tufted leaves. The glossy surfaced leaves are ovate to cordate-ovate and have nine (9) to eleven (11) vein pairs. Leaf dimensions are approximately nine and one-half (9½) inches to ten (10)inches long and six and one-half (6½) inches to seven (7) inches wide. Foliage height is approximately twenty (20) inches to twenty-four (24) inches and bears twenty-six (26) to thirty (30) white fragrant funnelform flowers, each three (3) to five (5) inches long, on a thirty (30) inch capitate raceme or rarely panicle. The dimensions and flower number are dependent on environmental conditions and cultural practices, and therefore may be slightly greater or smaller. In Michigan, the plant blooms from mid-August to mid-September.

The species *Hosta plantaginea* is quite uniform in appearance and does not have a large number of varieties or subspecies. The principal form of the plant is generally known by the species name *Hosta plantaginea*. Some variants that have been developed have been given distinct variety names. There appear to be two forms of the principal specie that is called *Hosta plantaginea*. These appear the same and are differentiated only by the size of the flower. One size is considered to be the normal or average form and the other is considered to be larger than normal. The present invention was derived from the normal form of the species known as *Hosta plantaginea*.

*Hosta plantaginea* is one of only two species of this genus that are native to, and only to, the mainland of China. The other species, *Hosta ventricosa*, flowers much before *Hosta plantaginea*, thus preventing any likelihood of interspecific cross pollination. All other species discovered to data have come from either the islands of Japan or a few from those of Korea. Being so geographically isolated, an intrabreeding species population will tend to become more identical.

*Hosta plantaginea* also has many traits consistent with a plant of a tetraploid nature (having twice the normal compliment of chromosomes). A natural doubling of the chromosomes would tend to produce a more homozygous population resulting in nearly identical appearing individuals.

The new variety has the characteristics of the original species but is distinctive from the original species in one main characteristic. The plant has basally-tufted, glossy surfaced leaves with a lighter variegated margin. The margin of each leaf has an irregular lacerated pattern frequently protruding toward the mid-rib. In areas where the margin tissue folds over the center green tissue an intermediate color results.

The colors of the plant have been determined by referral to the R.H.S. Colour Chart published by The Royal Horticultural Society of London. The intermediate color is a light pea-green, between Royal Horticultural Society Horticultural color chart Number 61/2 and 61/3. The margin emerges in the spring as a Dresden Yellow 64/3 and gradually lightens to white as the season progresses. The center of the leaf can be as light as a lettuce green 860 in nearly full sun in Michigan or as dark as between Scheeles Green 860/1 to Spinach Green 096/01 in deep shade and with good nutrition. The width of the margin varies with maturity from as narrow as one-sixteenth (1/16) inch to as much as three-quarters (¾) of an inch or more when mature. Environmental conditions, cultural practices and rate of growth also affect the extent, color, and width of the margin.

The growth of Hosta 'White Margin' is essentially the same as that of the parent variety of *Hosta plantaginea* species. The plant grows much better with ample water, but an established plant can withstand some brief periods of drought. Flowering is more prolific with more sun, but it produces ideal growth in Zeeland, Mich. with a few hours of light shade during the hottest part of the day. The plant is resistant to most major disease problems. The rhizomes survive sub-zero temperatures, but the foliage is not frost hard and can be affected by late spring frosts.

The variegation is a mutation of the outer layer of the meristem. This layer is sometimes referred to as the L-1 layer. As this layer forms the edge of the leaf and the petiole is also part of the leaf, in a monocot such as hostas the petiole expresses the same variegation. The color of the variegation in the petioles of the plant usually shows more yellowing as the petiole is in a more shaded area and not as lighted by the sun.

I claim:

1. The new and distinct variety of the plant *Hosta plantaginea* substantially as described and illustrated.

* * * * *